US010251822B2

(12) United States Patent
Schanbacher

(10) Patent No.: US 10,251,822 B2
(45) Date of Patent: Apr. 9, 2019

(54) METHODS AND COMPOSITIONS FOR TREATING CUTANEOUS FUNGAL INFECTIONS

(71) Applicant: Carl F. Schanbacher, Boston, MA (US)

(72) Inventor: Carl F. Schanbacher, Boston, MA (US)

(73) Assignee: Xeropedix, Inc., Boston, MA (US)

( * ) Notice: Subject to any disclaimer, the term of this patent is extended or adjusted under 35 U.S.C. 154(b) by 0 days.

(21) Appl. No.: 15/683,416

(22) Filed: Aug. 22, 2017

(65) Prior Publication Data

US 2018/0055745 A1    Mar. 1, 2018

Related U.S. Application Data

(60) Provisional application No. 62/380,787, filed on Aug. 29, 2016.

(51) Int. Cl.
| | | |
|---|---|---|
| *A61K 8/26* | (2006.01) | |
| *A61K 31/5375* | (2006.01) | |
| *A61K 31/145* | (2006.01) | |
| *A61K 31/415* | (2006.01) | |
| *A61K 31/4196* | (2006.01) | |
| *A61K 31/4164* | (2006.01) | |
| *A61K 31/4192* | (2006.01) | |
| *A61K 9/70* | (2006.01) | |
| *A61Q 15/00* | (2006.01) | |
| *A61K 31/137* | (2006.01) | |
| *A61K 8/02* | (2006.01) | |
| *A61K 47/10* | (2017.01) | |
| *A61K 9/14* | (2006.01) | |
| *A61K 33/06* | (2006.01) | |
| *A61K 8/34* | (2006.01) | |
| *A61K 9/08* | (2006.01) | |
| *A61K 9/00* | (2006.01) | |
| *A61P 17/00* | (2006.01) | |

(52) U.S. Cl.
CPC .............. *A61K 8/26* (2013.01); *A61K 8/022* (2013.01); *A61K 8/0208* (2013.01); *A61K 8/34* (2013.01); *A61K 9/0014* (2013.01); *A61K 9/08* (2013.01); *A61K 9/14* (2013.01); *A61K 9/70* (2013.01); *A61K 31/137* (2013.01); *A61K 31/145* (2013.01); *A61K 31/415* (2013.01); *A61K 31/4164* (2013.01); *A61K 31/4192* (2013.01); *A61K 31/4196* (2013.01); *A61K 31/5375* (2013.01); *A61K 33/06* (2013.01); *A61K 47/10* (2013.01); *A61P 17/00* (2018.01); *A61Q 15/00* (2013.01); *A61K 2800/87* (2013.01)

(58) Field of Classification Search
CPC .......... A61K 8/26; A61K 9/14; A61K 8/0208; A61K 8/022; A61K 9/70; A61K 47/10; A61K 8/34; A61K 31/137; A61K 9/0014; A61K 2800/87; A61K 31/5375; A61K 31/145; A61K 31/415; A61K 31/4196; A61K 31/4164; A61K 31/4192; A61K 33/06; A61K 9/08; A61Q 15/00; A61P 17/00

See application file for complete search history.

(56) References Cited

U.S. PATENT DOCUMENTS

| | | | |
|---|---|---|---|
| 4,083,954 A | | 4/1978 | Tsuchiya et al. |
| 4,551,330 A | * | 11/1985 | Wagman .................. A61K 8/19 424/59 |
| 5,143,718 A | | 9/1992 | Bar-Shalom |
| 5,468,473 A | * | 11/1995 | Mullen ..................... A61K 8/25 424/66 |
| 2003/0215408 A1 | | 11/2003 | Dees |
| 2005/0238672 A1 | * | 10/2005 | Nimni .................. A61K 9/0014 424/400 |
| 2006/0003649 A1 | * | 1/2006 | Runge .................. A61K 8/0208 442/59 |
| 2010/0056430 A1 | | 3/2010 | Lester |
| 2012/0061267 A1 | | 3/2012 | Villalobos |
| 2012/0114574 A1 | | 5/2012 | Touitou |

FOREIGN PATENT DOCUMENTS

| | | |
|---|---|---|
| EP | 2 191 828 A1 | 6/2010 |
| GB | 1024501 | 2/1963 |
| RU | 2 567 036 C1 | 10/2015 |

(Continued)

OTHER PUBLICATIONS

FM Tolnaftate 1% Spray (Jock) Powder, (2016), Perrigo Company, Safety Data Sheet, pp. 1-5. (Year: 2016).*

Aluminum Starch Octenylsucinate, [online]. EWG's Skin Deep Cosmetics Database, 2016 [retrieved on Sep. 15, 2018]. Retrieved from the Internet:<URL:https://www.ewg.org/skindeep/ingredient/700326/ALUMINUM_STARCH_OCTENYLSUCCINATE/#.WvM2KjbrtaQ>, (Year: 2016).*

Alberti, I. et al., "Effect of Ethanol and Isopropyl Myristate on the Availability of Topical Terbinafine in Human Stratum Corneum, in Vivo", International Journal of Pharmaceutics, vol. 219, 2001; pp. 11-19.

(Continued)

*Primary Examiner* — John Pak
*Assistant Examiner* — Andriae M Holt
(74) *Attorney, Agent, or Firm* — Proskauer Rose LLP

(57) ABSTRACT

The present invention relates to methods and compositions for the treatment of dermatophytic conditions such as tinea pedis. Such conditions can progress through multiple stages, such as fungal and bacterial stages, making effective treatment results difficult to achieve. The invention relates to a combined therapy effective for treatment of the condition that utilizes daily administration of a balanced combination of antifungals, antiperspirants and drying agents to achieve a beneficial therapeutic effect, irrespective of the stage of the disease upon commencement of the treatment.

14 Claims, No Drawings

(56) References Cited

FOREIGN PATENT DOCUMENTS

| WO | 2007/039533 A2 | 4/2007 |
| WO | 2010/086732 A1 | 8/2010 |

OTHER PUBLICATIONS

Alsterholm, M. et al., "Antimicrobial Activity of Topical Skin Pharmaceuticals—An In vitro Study"; Acta Derm Venereol 2010; vol. 90: pp. 239-245.
Bergstresser, P. R. et al., "Topical Terbinafine and Clotrimazole in Interdigital tinea Pedis: A Multicenter Comparison of Cure and Relapse rates with 1- and 4-week Treatment Regimens"; Journal of American Academy of Dermatology, vol. 28, No. 4; pp. 648-651.
Boboschko, I. et al., "Hyperhidrose als Risikofaktor der Tinea pedis", Der Hautarzt 2, Jan. 2005, pp. 151-154.
Brown, M. et al., "Efficacy, Tolerability and Consumer Acceptability of Terbinafine Topical Spray versus Terbinafine Topical Solution: A Phase IIa, Randomised, Observer-Blind, Comparative Study" Adis Am J. Clin Dermatol, MedSpra Non-Inferiority Clinical Trial, Jun. 6, 2013, pp. 1-7.
Ciftci, E. et al., "Mupirocin vs Terbinafine in Impetigo" Indian Journal of Pediatrics, vol. 69, Aug. 2002, pp. 679-682.
Crawford, F. et al., "Topical Treatments for Fungal Infections of the Skin and Nails of the Foot. (Review)" Cochrane Library—Cochrane Database of Reviews, 2016, pp. 1-161.
de Chauvin, M. F. et al., "Novel, Single-dose, Topical Treatment of Tinea Pedis using Terbinafine: Results of a Dose-finding Clinical Trial" The Authors, Journal Compilation 2007, Mycoses vol. 51, pp. 1-6.
Evans, E. G. V. et al., "Short-duration Therapy with Terbinafine 1% Cream in Dermatophyte Skin Infections", British Journal of Dermatology, 1994, vol. 130, pp. 83-87.
Field, L. A. et al., "Tinea Pedis in Athletes", International Journal of Dermatology, 2008, vol. 47, pp. 485-492.
GlaxoSmithKline Consumer Heathcare Holdings (US) LLC, Lamisil $^{AT}$® Terbinafine Hydrochloride Cream Package Information and Directions, 2007, pp. 1-4.
Gupta, A. K. et al., "Update in Antifungal Therapy of Dermatophytosis" Mycopathologia, 2008 vol. 166, pp. 353-367.
James, I. G. et al., "Short-duration Topical Treatment of Tinea Pedis using Terbinafine Emulsion Gel: Results of a Dose-ranging Clinical Trial" Journal of Dermatological Treatment, Informa HealthCare, 2007, vol. 18, pp. 163-168.
Koca et al., "Interdijital Tip Tinea Pedis'te Klotrimazol ve Alüminyum Hidroksiklorid Kombinasyon Tedavisinin, Klotrimazol Tedavisi İle Karş ilaş tirtlmasi" O.N.Ü. Tip Dergisi, 2001, vol. 18(3), pp. 192-197, including partial translation.
Korting, H. C. et al., "Comparable Efficacy and Safety of Various Topical Formulations of Terbinafine in Tinea Pedis Irrespective of the Treatment Regimen: Results of a Meta-Analysis", Am J Clin Dermatol 2007, vol. 8(6), pp. 357-364.
Leyden, J. J. et al., "Aluminum Chloride in the Treatment of Symptomatic Athlete's Foot" Arch Dermatol—vol. 111, Aug. 1975, pp. 1004-1010.
Leyden, J. L., "Tinea Pedis Pathophysiology and Treatment" Journal of the American Academy of Dermatology, Sep. 1994, vol. 31, Issue 3, Part 2, pp. S31-S33.
Nolting, S. et al., "Clinical Relevance of the Antibacterial Activity of Terbinafine: A Contralateral Comparison between 1% Terbinafine Cream and 0-1% Gentamicin Sulphate Cream in Pyoderma", British Journal of Dermatology, 1992, vol. 126, Supplement 39, pp. 56-60.
Pranteda, G. et al., "Pitted Keratolysis, Erythromycin, and Hyperhidrosis" Dermatologic Therapy, vol. 27, 2014, pp. 101-104.
Rand, S., "Overview: The Treatment of Dermatophytosis" J Am Acad Dermatol, vol. 43, No. 5, Nov. 2000, vol. 43, pp. S104-S112.
Savin R. C., "Treatment of Chronic Tinea Pedis (Athlete's Foot Type) with Topical Terbinafine" J Am Acad Dermatol, vol. 23, No. 4, Part 2, Oct. 1990, vol. 23, pp. 786-789.
Walling, H. W., "Primary Hyperhidrosis Increases the Risk of Cutaneous Infection: A Case-control Study of 387 Patients" J Am Acad Dermatol, vol. 61, No. 2, pp. 242-246.
Katz et al "Topical Antifungal Agents" Current Problems in Dermato, Mosby, vol. 12, No. 5, XP005466380, ISSN: 1040-0486, DOI: 10.1016/S1040-0486(00)80004-6, Tables 1 and 3, Sep. 2000 (Sep. 2000), pp. 226-229.
Leyden, J.J. et al., "Aluminum Chloride in the Treatment of Symptomatic Athlete's Foot" XP002775888, Database Accession No. EMB-1977026945, Archives of Dermatology, ISSN: 0003-987X, vol. 111, No. 8, 1975, pp. 1004-1010.
International Searching Authority, International Search Report for International Application No. PCT/US2017/047971, dated Dec. 15, 2017, pp. 1-8.
Aspres et al., "Predictive Testing for Irritancy and Allergenicity of Tea Tree Oil in Normal Human Subjects" Exogenoous Dermatology, 2003, vol. 2, pp. 258-261.
Brennan et al., Overview of Topical Therapy for Common Superficial Fungal Infections and the Role of New Topical Agents Journal of American Academy of Dermatology, Feb. 1997, pp. S3-S8.
Cross, et al., "Human Skin Penetration of the Major Components of Australian Tea Tree Oil Applied in its Pure Form and as a 20% Solution in Vitro" European Journal of Pharmaceutics and Biopharmaceutics, vol. 69, 2008, pp. 214-222.
Federal Register, Proposed Rules, vol. 47, No. 56, Mar. 23, 1982, pp. 12541-12544.
Griffin et al., "An Agar Dilution Method for the Determination of the Minimum Inhibitory Concentration of Essential Oils" (Link: http://dx.doi.org/10.1080/10412905.2000.9699509), Journal of Essential Oil Research, vol. 12, No. 2, pp. 249-255, Year: 2000.
Husni et al., "Effect of Extraction Methods on Antifungal Activity of Sea Cucumber (*Stichopus japonicus*)" Agrithech, vol. 34, No. 1 Feb. 2014, pp. 1-7.
Schmook, et al., "Comparison of Human Skin or Epidermis Models with Human and Animal Skin in In-Vitro Percutaneous Absorption" International Journal of Pharmaceutics, vol. 215, 2001, pp. 51-56.
Seo, et al., "In Vitro Skin Absorption Tests of Three Types of Parabens using a Franz Diffusion Cell" Journal of Exposure Science and Environmental Epidemiology, 2016, pp. 1-6.
Sigma, Product Information for Polymyxin B Sulfate, Jul. 7, 1997, pp. 1-2.
Soni et al., "Evaluation of the Health Aspects of Methyl Paraben: A Review of the Published Literature" Food and chemical Toxicology vol. 40, 2002, pp. 1335-1373.
Soni et al., "Safety Assessment of Esters of P-Hydroxybenzoic Acid (Parabens)" Food and Chemical Toxicology, vol. 43, 2005, pp. 985-1015.
Syed et al., "Treatment of Toenail Onychomycosis with 2% Butenafine and 5% *Melaleuca alternifolia* (Tea Tree) Oil in Cream" Tropical Medicine and International Health, vol. 4, No. 4, Apr. 1999, pp. 284-287.
Tong, et al., "Tea Tree Oil in the Treatment of Tinea Pedis" Australas J. Dermatol, 1992, vol. 33, pp. 145-149.
Weiss et al., "Solubility of Antibiotics in Twenty-four Solvents: Use in Analysis" Antibiotics and Chemotherapy vol. 1, No. 7, Jul. 1957, pp. 374-377.
Whitton et al., "The Thickness of the Epidermis" British Journal of Dermatology, 1973, vol. 89, pp. 467-476.

\* cited by examiner

METHODS AND COMPOSITIONS FOR TREATING CUTANEOUS FUNGAL INFECTIONS

RELATED APPLICATIONS

This application claims benefit to U.S. Provisional Patent Application Ser. No. 62/380,787, filed Aug. 29, 2016, the contents of which are incorporated herein in their entirety.

FIELD OF THE INVENTION

The present invention generally relates to compositions and methods for treatment of cutaneous fungal infections including tinea pedis, tinea corporis, and tinea cruris.

BACKGROUND

Until the 1940s, there were few treatments of any kind for tinea pedis (athlete's foot). Spurred by the prevalence of dermatophytoses among military personnel during the wars of the mid-twentieth century, the search for truly effective treatments began. Azole antifungals were first synthesized in the late 1960s, and over the next two decades, research and development focused on this class of treatments, representing a major breakthrough in the targeted treatment of fungal infections. Further progress was made with the development of potent fungicidal allylamines in the 1990s. Today, one such allylamine, terbinafine, remains the most potent treatment for tinea infections. Terbinafine is the most effective topical agent against tinea pedis (Crawford & Hollis, Cochrane Database of Systematic Reviews 2007, Issue 3. Art. No.: CD001434). Unlike fungistats, which require up to four weeks of application, terbinafine is effective in a shorter course of treatment. Current labeling guidelines for terbinafine cream call for twice-daily application for 1-2 weeks (Lamisil AT® Drug Facts, GlaxoSmithKline Consumer Healthcare Holdings, 2017).

By comparison, antiperspirant treatment for tinea pedis has received relatively little academic attention. The only notable example of an antiperspirant treatment for tinea pedis comes from a 1975 study by Leyden & Kligman (Arch Dermatol, Vol. 111, p. 1004, August, 1975). They found that a 30% aluminum chloride solution was effective at reducing unpleasant symptoms of tinea pedis. However, this treatment did not resolve the infection entirely; instead, it transformed the macerated, malodorous form of tinea pedis associated with bacterial co-infection (sometimes called dermatophytosis complex) back into the dry, scaly type that indicates a purely fungal infection (dermatophytosis simplex). Because of the focus on the development of antifungals that promised to treat the underlying cause of tinea pedis, there has been little further research on the use of antiperspirants in the treatment of tinea pedis. In 2001, Koca et al. (O.M.Ü. Tip Dergisi Cilt: 18 No. 3, p. 192, 2001) conducted a study on a combination antiperspirant-antifungal therapy. Patients were instructed to apply cream containing clotrimazole (a fungistatic azole antifungal) in the morning, and aluminum chlorohydrate cream in the evening. The researchers found no benefit from the addition of an antiperspirant compared to antifungal therapy alone.

Dees (U.S. Pat. No. 7,201,914) describes combining an antiperspirant with an antimicrobial for the treatment of acne. Dees does not describe any standard topical antifungal agents as examples of antimicrobial agents. Lester (U.S. Pat. Publication No. 2010/0056430) describes reducing foot odor using antibacterials with other ingredients such as terbinafine and aluminum chloride, but Lester did not combine his materials with an alcohol drying agent or use them in combination for treatment of infections such as dermatophytosis. Villalobos (U.S. Pat. Publication 2012/0061267) describes using a terbinafine wipe with alcohol. Villalobos does not use an antibacterial or an antiperspirant compound and failed to demonstrate efficacy.

What is needed is an effective therapy that can be applied for the efficient treatment of dermatophytic infections irrespective of the stage of the infection.

SUMMARY OF THE INVENTION

A problem in the prior art was that previous compositions overlooked the positive impact antiperspirants can have on treating symptomatic fungal infections. Additionally, the benefit of combining a suitable antiperspirant with a suitable antifungal and the resulting synergism that provides an accelerated therapeutic effect were also unrecognized. Moreover, the significance of the proper treatment vehicle for patient compliance and treatment success cannot be understated.

The present invention is directed to compositions and methods comprising an antifungal agent and an antiperspirant to treat tinea pedis and other fungal infections such as tinea cruris. The antifungal agent and the antiperspirant complement each other and offer a significantly better treatment than either would on its own.

One preferred embodiment of the present invention comprises the combination of an antifungal agent, an antiperspirant, a solvent, and a vehicle for solution delivery. The antiperspirant (aluminum chloride hexahydrate) and solvent (aqueous ethanol) work synergistically: the antiperspirant reduces sweat and the solvent dehydrates the skin, creating a dry environment that makes it harder for fungi and bacteria to grow. This activity complements the antifungal's action against the fungi as well as the antibacterial properties of the antiperspirant and the solvent.

The compositions of the present invention are more effective in treating tinea pedis than previous compositions, and overcome deficiencies of prior conventional methods used to treat tinea pedis.

In one aspect, the invention includes a method for treating a dermatophytic infection. The method can include the steps of topically applying an antifungal, topically applying an antiperspirant comprising an aluminum salt, topically applying a solvent vehicle comprising an alcohol, where the antifungal, the antiperspirant and the solvent vehicle are all applied during a single administration event, and repeating the administration event not more than about daily.

Embodiments of the invention include using a fungicidal antifungal, and the fungicide can be an allylamine. A suitable fungicide is terbinafine, or a pharmaceutically acceptable salt thereof. In some embodiments the antifungal is a fungicide that includes at least one of amorolfin, butenafine, naftifine, terbinafine or tolnaftate, or pharmaceutically acceptable salts thereof. Preferable, the method is repeated until the infection is resolved, and resolution of the infection can be determined using the KOH (potassium hydroxide) microscopy test for the presence of a fungus.

In some embodiments the antiperspirant of the method is or comprises aluminum chloride hexahydrate. The solvent vehicle can either include or be ethanol (ethyl alcohol). Duration of the treatment can range between one and four weeks, for example depending upon treatment efficacy. Daily administrations are preferred, as this can prevent overdrying of the treated area. Other antifungals can be used with the invention. As such, the method can include the use of the following antifungals: an azole, including at least one of clotrimazole, ketoconazole, fluconazole, flutrimazole, itraconazole, bifonazole, butoconazole, econazole, fenticonazole, isoconazole, luliconazole, miconazole, omoconazole, oxiconazole, sertaconazole, sulconazole, tioconazole, tiabendazole, croconazole, chlormidazole, neticonazole, terconazole, posaconazole, voriconazole, albaconazole, isavuconazole, eberconazole, or efinaconazole; or a polyene, including at least one of amphotericin B, nystatin, hamycin, and natamycin; or at least one of nystatin, natamycin, hachimycin, pecilocin, mepartricin, pyrrolnitrin, griseofluvin, bromochlorosalicylanilide, methylrosaniline, tribromometacresol, undecylenic acid, polynoxylin, 2-(4-chlorophenoxy)-ethanol, chlorphenesin, ticlatone, sulbentine, ethyl para-hydroxybenzoate, haloprogin, selenium sulfide, ciclopirox, dimazole, flucytosine, benzalkonium chloride, benzoyl peroxide, benzoic acid, salicylic acid, tannic acid, boric acid, gentian violet, chlorhexidine, cetylpyridinium chloride, tolciclate, sodium thiosulfate, potassium iodide, tea tree oil, citronella oil, lemongrass oil, garlic, vinegar, tavaborole, abafungin, an echinocandin (caspofungin, micafungin, and anidulafungin), nikkomycin, a pradimicin, or a benanomycin; or pharmaceutically acceptable salts thereof.

Another aspect of the invention relates to a composition for treatment of a dermatophytic infection, the composition comprising an antifungal, an antiperspirant drying agent that includes an aluminum salt, and a cream-free solvent vehicle comprising an alcohol for delivery of the antifungal and the drying agent. The antifungal, preferably, is a fungicide, which can be terbinafine, or a pharmaceutically acceptable salt thereof.

Compositions of the invention also include a fungicide that includes at least one of amorolfin, butenafine, naftifine, terbinafine or tolnaftate, or pharmaceutically acceptable salts thereof. The composition can be administered via a wipe, or a "towlette," e.g., from a sealed, disposable, tear-away package or packet. One disposable wipe packet can be opened and used on a daily basis to effectively treat the condition, and a second packet used on the second day, etc., until the infection is resolved. This treatment duration may only need to be for about a week (e.g., seven packets/administrations), or for some situations two to four weeks of treatment (on a daily basis) may be required.

Compositions of the invention include terbinafine present in an amount of between 0.5 and 10% of the composition by weight. The aluminum salt (e.g., aluminum chloride hexahydrate) can be present in an amount of not more than about 30% by weight (of the composition). In some embodiments, the aluminum salt amount is reduced to between about 15 and 20% by weight. A preferred antiperspirant is aluminum chloride hexahydrate ($AlCl_3.6H_2O$).

Yet another aspect of the invention includes a solution for treating a dermatophytic infection that can be produced by the following process. Terbinafine (or pharmaceutically acceptable salts thereof) is added to a liquid solvent solution that either is or includes ethanol. A measured amount of aluminum chloride, such as crushed $AlCl_3.6H_2O$, is added to the solution, then the solution is made up, e.g., with additional ethanol, to an aluminum chloride concentration of about 200 gm/liter, and a terbinafine concentration of about 10 gm/liter of the solution. Preferable, the terbinafine and the AlCl3 are thoroughly dissolved to create a uniform solution. The solution can be added to a wipe for eventual treatment of a patient, such as for a dermatophytic condition. The wipe can be stored in a packet, as described above.

Embodiments include producing the solution using terbinafine that is provided as a powder, and the amount added can be not in excess of about 100 gm/liter. Embodiments also include having AlCl3 present in an amount of not more than about 300 gm/liter of the solution.

Another aspect of the invention includes a kit embodying the invention. The kit can include an article or a container that includes an antiperspirant comprising an aluminum salt dissolvable in an alcohol solvent, such as a solvent including an alcohol (such as ethanol), in an amount of about 200 gm/liter, a fungicide dissolvable in the solution, and the alcohol solvent. The fungicide and the antiperspirant can be dissolved in the alcohol solvent to form a solution, and the container be used to house the article.

In embodiments of the kit the fungicide includes at least one of orolfin, butenafine, naftifine, terbinafine or tolnaftate, or pharmaceutically acceptable salts thereof. The kit can also include an applicator, such as a wipe and/or a roller ball. In some embodiments the kit includes at least 7 wipes for administration of the solution, and each wipe can be packaged separately, e.g., for daily use. The kit can also include a calendar and/or an instruction set, the calendar for tracking a daily administration of a treatment of how the materials of the kit are being used.

DETAILED DESCRIPTION

Although antifungals have proven to be effective in terms of their ability to eliminate fungi, their clinical effectiveness in the treatment of tinea pedis is not impressive. Interdigital tinea pedis is, in many cases, not solely a fungal infection, and is therefore harder for antifungals alone to address. Fungal hyphae permeate the stratum corneum, weakening it and thus weakening the skin's defenses against further infection. Fungi also produce penicillin- and streptomycin-like substances. In this environment, penicillin-resistant bacteria proliferate, producing proteolytic substances, breaking down the tissue of the interdigital skin, resulting in maceration and leukokeratosis. These bacteria also produce sulfur compounds, which are potent natural antifungal agents. In these cases, the bacterial co-infection can actually eliminate the primary fungal infection; however, because the stratum corneum of the interspace has been weakened and a bacterial infection has taken root, the bacterial infection persists in the fungi's absence, preventing the stratum corneum from healing. In this stage of the disease, antifungal treatment alone is of limited effect, because the bacterial infection has become the primary issue.

These cases of tinea pedis may be significantly underrepresented in clinical trials. Because the bacteria have a natural antifungal effect, severe cases of tinea pedis that have reached the complex co-infection stage often give negative results on potassium hydroxide and culture tests, which are used to identify fungal infections. It is estimated that fungi are recovered in as little as one third of symptomatic interspaces (Leyden, J Am Acad Dermatol, Vol. 31, Issue 3, Part 2, 1994, p. S31). However, clinical trials to test the efficacy of antifungal drugs, which were common in the second half of the twentieth century, almost always required confirmation of fungal infection with both tests. This meant that tinea pedis patients whose disease had progressed to the point of bacterial superinfection would be underrepresented in these studies, because the severity of the infection resulted in the inability to confirm the presence of fungi in the test. Thus, studies that focused on antifungal efficacy likely overestimated the clinical effectiveness of the drugs, because a significant portion of tinea pedis patients were not included, and these patients suffered from a particularly unpleasant form of tinea pedis that antifungals would be unlikely to treat effectively.

Antifungals and antiperspirants are two effective and complementary weapons against tinea pedis and other dermatophytic infections. Antifungals are designed to eliminate fungi, either through destruction of the organisms (fungicide) or through preventing further fungal growth (fungistasis), allowing the skin to shed fungi with time. An antiperspirant can complement the action of an antifungal in two ways: by drying the skin and by killing bacteria. Antiperspirants can dry the skin in two ways: firstly, by precipitating plugs that obstruct sweat glands, preventing moisture from reaching the skin, and secondly, by acting as astringent agents, causing tissue to contract, which diminishes the skin's capacity to hold water and narrows the pores. Both fungi and bacteria thrive in wet environments like the foot (particularly the interdigital spaces), so the benefit of reduced moisture is significant. Indeed, epidemiologists have found that occlusive footwear is one of the most significant risk factors for tinea pedis, because it traps heat and moisture around the foot, providing an ideal environment for microbial growth.

The second beneficial aspect of aluminum-based antiperspirants is their antibacterial activity. Aluminum-based antiperspirants have been shown to have in vitro as well as in vivo antibacterial effects, indicating successful antibacterial action independent of the antimicrobial effect of drying the skin. This antibacterial effect serves to supplement the drying effect; however, we believe that the drying effect is the primary mechanism that makes this treatment effective against tinea pedis. For example, in their study of aluminum salts as treatments for tinea pedis, Leyden & Kligman found that aluminum chlorohydrate, a potent antibacterial agent but ineffective astringent, was less effective than aluminum chloride, which is less antibacterial but more astringent, indicating that moisture reduction rather than antibacterial activity is the primary mechanism through which antiperspirants alleviate the symptoms of tinea pedis.

Recent research has raised the possibility that the role of perspiration in tinea pedis and other dermatophytoses may be even more significant than previously understood. Several studies have found a link between plantar hyperhidrosis (excessive sweating of the feet) and tinea pedis. Researchers have generally hypothesized a causal link in one direction, i.e., those with preexisting hyperhidrosis are at greater risk for developing tinea pedis. However, recent research into pitted keratolysis, a bacterial infection of the foot, strongly suggests that hyperhidrosis is triggered by the infection, rather than vice versa (Pranteda et al., Dermatologic Therapy, Vol. 27, p. 101, 2014). The authors theorize that the skin's inflammatory response to the infection prompts increased function of the sweat glands. It seems possible that a similar dynamic is at play in dermatophytoses. This model would indicate a vicious cycle, in which infection increases sweating, and this excess moisture creates conditions for the infection to become entrenched and intensify. If such a dynamic does take place, it would reinforce the role of antiperspirants in the successful treatment of tinea pedis, emphasizing the significance of the moist environment in the development of the infection.

The present invention is directed to compositions comprising an antifungal agent, an antiperspirant, and a vehicle to treat tinea pedis and other fungal infections such as tinea cruris. The antifungal agent and the antiperspirant complement each other and offer a significantly better treatment than either can provide alone. The antiperspirant complements the action of the antifungal in two ways: by drying the skin and killing bacteria. However, care must be taken to prevent overdrying of the skin during treatment, which can cause its own set of problems. The invention is intended to reduce excess moisture due to sweating, but if applied too frequently, it can cause the skin to dry out, which exacerbates some of the symptoms of tinea pedis, including erythema and desquamation. Furthermore, excessive dryness may prevent the skin from healing once the infection has been resolved, leaving the skin vulnerable to new infection once treatment stops. Administration of the drying agent not more than once daily appears to be particularly effective, as detailed below. The vehicle can complement the activity of the active ingredients. Because of the antibacterial properties of the antiperspirant (and of some vehicles), the compositions of the present invention offer advantages over treating tinea pedis using antifungals alone, because many cases of tinea pedis involve a bacterial co-infection. This invention is also advantageous against fungal infections, because the drying effect of the antiperspirant and alcohol vehicle is inimical to fungal growth. Proper selection of an antifungal (e.g., a fungicide), an antiperspirant, and a drying solvent vehicle can result in a composition that is effective for the treatment of dermatophytic conditions regardless of the stage of the infection.

Antifungal Component

Antifungals are drugs that selectively eliminate fungal pathogens with minimum toxicity to the host. Extant antifungal therapies for tinea pedis can come in topical or systemic form. Systemic treatment is associated with a risk of hepatotoxicity; therefore, topical treatment is usually preferred for its safety profile, with systemic treatment pursued in cases where topical treatment is ineffective. Typical drug regimens are usually between 1-4 weeks. Different classes of antifungals target specific functions of the fungal cells.

Most common antifungal agents function by interfering with ergosterol, a vital component of fungal cell membranes. Polyenes, the first drugs developed to treat fungal infections, bind directly with ergosterol, forming channels through which small molecules are able to leak out of the cell, leading to cellular death. Drugs that belong to this class include amphotericin B, nystatin, hamycin, and natamycin. The drawback of polyenes is their toxicity: they tend to bind to other sterols, including cholesterol in humans. Today, they are used mostly as topical treatments against *Candida* species.

Azole antifungals, the first to achieve widespread success, work by bonding to the enzyme lanosterol 14α-demethylase, which is essential in converting lanosterol into ergosterol. The fungal cells, unable to produce ergosterol, are unable to remain intact and reproduce, and are shed from the skin. This is a fungistatic mechanism, meaning that fungal growth is impeded but fungi are not immediately killed, and instead patients must wait for the skin to shed its infected stratum corneum. This means that treatment with azoles typically requires longer treatment regimens (four weeks, in many cases) and strict adherence. Well-known azoles include clotrimazole, ketoconazole, fluconazole, flutrimazole, itraconazole, bifonazole, butoconazole, econazole, fenticonazole, isoconazole, luliconazole, miconazole, omoconazole, oxiconazole, sertaconazole, sulconazole, tioconazole, tiabendazole, croconazole, chlormidazole, neticonazole, terconazole, posaconazole, voriconazole, albaconazole, isavuconazole, eberconazole, and efinaconazole.

Unlike fungistatic azoles, allylamine antifungals are primarily fungicidal. These compounds inhibit a different enzyme, squalene epoxidase, which is an essential part of an earlier stage of ergosterol biosynthesis. Like azoles, this leads to ergosterol deficiency; however, allylamines also lead to a toxic accumulation of squalene in the cell, causing more rapid cell death. The fungicidal action of allylamines allows for shorter and more effective therapies: they can be effective even in a single dose, and are less likely to see a relapse after a short course of therapy. Allylamines administered topically include amorolfin, butenafine, naftifine, and terbinafine. Available since the 1990s, terbinafine has become the drug of choice in most cases of tinea pedis, in large part because its shorter treatment regimen leads to increased compliance rates. Preferred embodiments of the invention use fungicides, and allylamines in particular. Terbinafine has been found to be particularly effective.

Tolnaftate is a synthetic thiocarbamate used frequently to treat tinea pedis. Its exact mechanism of action is not entirely known, but it is believed that tolnaftate interferes with the function of squalene epoxidase, much like allylamines.

Other chemical agents are used as antifungals, including nystatin, natamycin, hachimycin, pecilocin, mepartricin, pyrrolnitrin, griseofluvin, bromochlorosalicylanilide, methylrosaniline, tribromometacresol, undecylenic acid, polynoxylin, 2-(4-chlorophenoxy)-ethanol, chlorphenesin, ticlatone, sulbentine, ethyl para-hydroxybenzoate, haloprogin, selenium sulfide, ciclopirox, dimazole, flucytosine, benzalkonium chloride, benzoyl peroxide, benzoic acid, salicylic acid, tannic acid, boric acid, gentian violet, chlorhexidine, cetylpyridinium chloride, tolciclate, sodium thiosulfate, and potassium iodide. Natural remedies are also used as antifungals, tea tree oil, citronella oil, lemongrass oil, garlic, and vinegar. Finally, new agents such as tavaborole, abafungin, echinocandins (caspofungin, micafungin, and anidulafungin), nikkomycins, pradimicins, and benanomycins may prove to be useful in the treatment of fungal infections, including tinea pedis.

Embodiments of the invention can include any of the antifungal components listed above. The preferred embodiment utilizes terbinafine, the most effective antifungal currently available.

Antiperspirant Component

All compounds approved by the FDA for use in over-the-counter antiperspirants are aluminum salts, sharing a common mechanism for sweat reduction. Aluminum salts function by obstructing the distal sweat gland duct. They complex with sweat duct keratin and mucopolysaccharides, damaging the sweat duct cuboidal cell lining and forming a polymeric gelatinous cast, which obstructs sweat passage. Sweat production is not shut off; rather the sweat gland, which resides in the reticular dermis and adipose tissues, continues to produce sweat, although the production is greatly reduced due to obstruction of the normal egress route via the aluminum salt complex within the distal sweat duct. It has been noted that the aluminum salt plug may extend down into the secretory coils within the adipose tissue. With long-term aluminum antiperspirant application, secretory cells within the sweat gland are often damaged, with resulting decreased sweat production. Sweat production eventually returns as the cast eventually breaks down.

In some embodiments of the invention, the antiperspirant component can be aluminum chloride, aluminum chlorohydrate, aluminum chlorohydrex polyethylene glycol complex, aluminum chlorohydrex propylene glycol complex, aluminum dichlorohydrate, aluminum dichlorohydrex polyethylene glycol complex, aluminum dichlorohydrex propylene glycol complex, aluminum sesquichlorohydrate, aluminum sesquichlorohydrex polyethylene glycol complex, aluminum sesquichlorohydrex propylene glycol complex, aluminum sulfate buffered, aluminum zirconium octachlorohydrate, aluminum zirconium octachlorohydrex glycine complex, aluminum zirconium pentachlorohydrate, aluminum zirconium pentachlorohydrex glycine complex, aluminum zirconium tetrachlorohydrate, aluminum zirconium tetrachlorohydrex glycine complex, aluminum zirconium trichlorohydrate, or aluminum zirconium trichlorohydrex glycine complex. Non-aluminum antiperspirants are also commercially desirable due to public concern over the health effects of aluminum intake, although they are often less effective antiperspirants than aluminum salts. Examples of non-aluminum antiperspirants include peptides, methenamine, tannins, and other astringent agents, as well as titanium salts. This invention focuses on aluminum-based antiperspirants due to their proven track record of efficacy and the current scientific understanding that aluminum-based antiperspirants are not linked to an increased risk of cancer or other negative health effects.

In a preferred embodiment, the antiperspirant is aluminum chloride hexahydrate ($AlCl_3 \cdot 6H_2O$), the hydrated form of aluminum chloride. Aluminum chloride hexahydrate is typically used in concentrations of 10-30% in water, aqueous alcohol, or anhydrous alcohol. Higher concentrations are more irritating to the skin. Aluminum chloride hexahydrate also possesses astringent and antimicrobial properties that can be useful in the composition of the present invention.

Vehicles

The vehicle is used to deliver the active ingredients (antifungal and antiperspirant) to the skin. The vehicle can be selected to enhance or complement the qualities of the active ingredients. In this invention, alcohol-based vehicles are preferred. Alcohols dry quickly, leaving behind no residue, which has aesthetic benefits and contributes to the dryness of the skin. Of particular interest is ethanol (ethyl alcohol).

Ethanol possesses several beneficial properties that can be useful in the composition of the present invention including antimicrobial activity, percutaneous penetration enhancement, and quick evaporation. Ethanol is a well-known antimicrobial, widely used for skin disinfection. Additionally, ethanol tends to dehydrate the skin, which can create an environment inimical to fungal growth. In certain embodiments of the invention, the amount of ethanol in the vehicle may be limited to prevent overdrying of the skin, which may lead to irritation. Ethanol is also advantageous in that it evaporates quickly, which makes it more pleasant than other dermatological vehicles that dry slowly or leave residue behind. Even though ethanol has a tendency to produce a burning sensation, familiar to those who have used rubbing alcohol on a cut or aftershave after shaving, its benefits outweigh this drawback.

Studies that have used ethanol-based vehicles for tinea pedis have reported minimal complaint about burning sensation from patients. Ethanol lowers the threshold temperature at which the transient receptor potential vanilloid 1 (TRPV1) cation channel sends a signal to the brain indicating excessive heat from approximately 42° C. to 34° C. This new threshold temperature is below the core body temperature of 37° C., so normal body temperature causes TRPV1 to produce a burning sensation. However, the average foot temperature is between 30° C. and 34° C., so the burning sensation experienced from ethanol application to the foot is minimal.

Studies have shown that ethanol can enhance percutaneous penetration. In vivo studies indicate that percutaneous terbinafine absorption is enhanced in ethanol solution compared to isopropyl myristate solution (Alberti et al., International Journal of Pharmaceutics, Vol. 219, p. 11, 2001). Furthermore, ethanol gel has been shown to improve terbinafine's rate of absorption, maximum concentration, and half-life in the skin compared to a standard cream formulation (James et al., Journal of Dermatological Treatment, Vol. 18, p. 163, 2007). This enhancement allows for decreased treatment frequency and/or duration of therapy compared to cream.

The vehicle can include additional components to enhance different qualities of the invention. The addition of a stabilizer or preservative can improve the invention's stability. Similarly, solvents like water and propylene glycol and surfactants can help the solution remain well dispersed. Fragrances can improve the aesthetic qualities of the invention. Other ingredients could be added to the vehicle to slow the release of active ingredients, allowing for less frequent application, or to increase the penetration of the active ingredients.

Emollients (including silicones, oils, alcohols, and petrolatum) be used to improve experiential qualities and decrease the risk of overdrying; however, these ingredients must be judiciously selected to avoid counteracting the intended drying effect of the invention. The counterproductive moisturizing effect of cream-based vehicles may be partly to blame for the failure of previous antiperspirant treatments for tinea pedis, including the study on clotrimazole-aluminum chlorohydrate combination therapy conducted by Koca et al. Several problems have been identified with the treatment used in this study. Since patients were subject to twice-daily application, the moisturizing cream vehicle used by Koca inhibited the crucial drying effect of the antiperspirant. Additionally, the specific antifungal and antiperspirant used were less effective against tinea pedis than other antifungals and antiperspirants. This study is yet another reason antiperspirant treatment of tinea pedis has previously been determined to not be effective for tinea pedis. Indeed, in the systematic review of topical treatments for tinea pedis by Crawford & Hollis, the Koca study was excluded even from consideration because the experimental agent included an antiperspirant.

Form of the Composition and its Application

The active ingredients (namely, the antifungal and the antiperspirant) and the various vehicles can be delivered to the skin in a variety of different forms. Example compositions of the invention include liquid solution, spray, solid stick, gel, film-forming solution, ointment, liquid bath, powder, lotion, and cream. Preferred embodiments of the invention include or use ethanol as a solvent vehicle. Ethanol is preferred over oil- and water-based cream formulations due to its increased drying activity. Liquid forms can be applied by wiping or rubbing on the appropriate body part, such as the feet, or by bathing the body part in the solution. Spray can be sprayed directly onto the skin. The solid stick can be applied using a rubbing motion on the skin. The powder can be sprinkled into a pair of shoes before putting them on or sprinkled directly onto the skin. Additionally, the compound can be incorporated into articles of clothing during manufacture. In all cases, the invention should be applied so that the active ingredients reach the affected area. In some embodiments, the invention is to be applied to the bottom and sides of both feet. Studies have shown that this technique is effective at preventing reinfection, as fungi may have imperceptibly infected other parts of the foot, and are later transferred back to the region of the original infection when not treated. It is contemplated that the compositions of the present invention can be applied to the foot at room temperature. The compositions should be applied to clean and dry feet. In one embodiment the composition is applied before bed.

Active ingredient concentrations can be chosen to deliver the most effective treatment with the best safety profile. The antifungal component can be used in a concentration of about 0.1% to 20%, i.e., 1 to 200 gm/liter of solution. Preferred embodiments have not more than 10% terbinafine. The antiperspirant can be used in a concentration of about 0.1% to about 30% of $AlCl_3$, i.e., not more than about 300 gm of $AlCl_3$ per liter of solution. In the preferred embodiment, the antifungal (terbinafine) is present at a concentration of about 1%, the antiperspirant (aluminum chloride hexahydrate) is present at a concentration of about 15-20%. The compositions of the present invention can be adjusted to treat other microbial infections where moisture due to sweat is a contributing factor, such as bacterial and fungal infections of the foot, armpit, or groin.

A significant advantage of this invention over existing treatments for dermatophytosis is reduced treatment frequency. One of the primary causes of treatment failure with existing treatments is poor adherence. Patients discontinue treatment before the fungus is successfully eradicated because twice-daily application of an oily cream is inconvenient and unpleasant. Because of the synergistic effects of the combination therapy, which makes the active ingredients more effective than either would be on its own, less frequent treatment is possible. Once-daily application is the standard regime for this invention, but even less frequent treatment may be possible. Patients are more likely to adhere to a less burdensome treatment schedule, so there is a greater likelihood that the fungus will be successfully eradicated with this invention.

Wipe Embodiment

Embodiments of the invention use disposable wipes to apply the composition to the affected area of the skin, a novel delivery mechanism in the treatment of tinea pedis. This new topical application represents a significant step forward in the treatment of tinea pedis, where a large proportion of treatment failures are due to patient non-compliance rather than non-efficacy of treatment (de Chauvin et al., Mycoses, Vol. 51, p. 1, 2007). The wipe embodiment offers benefits in terms of dosing assistance, cleaning, and convenience.

Materials & Manufacture in a preferred embodiment, wipes are a disposable non-woven polyester-viscose blend, which is more absorbent than polyester alone. Any combination of man-made and/or natural fibers could be used, with the caveat that it may be necessary to adjust the formulation or volume of solution to ensure proper delivery of active ingredients. For example, a less-absorbent 100% polyester wipe may need to be saturated with a more concentrated solution to deliver the proper dose of active ingredients. Pharmacokinetic testing can be used to ensure that an appropriate dose of active ingredients is successfully deposited on the skin.

The untreated wipes can be folded and inserted into individual pouches (which are sealed on three sides and open on one side). The pouches can be metal-laminated polyethylene with a notch at the side to enable easy tearing. Other individual pouch materials, including foil-laminated paper or un-laminated polyethylene, are possible. Alternatively, the wipes may be packaged in a resealable container rather than individual pouches. In this case, the solution will need to be formulated to ensure that all wipes remain properly saturated.

The liquid solution, which contains the active ingredients, is added to the pouch, and the pouch is sealed on its open side. If necessary, pressure can be applied to the pouch to assure adequate saturation throughout the wipe. The packaging process can be accomplished by a packaging machine, or can be done by hand when small quantities are required.

Application

To use the wipe, the end of the package should be torn off to open it, the wipe should be unfolded, and patients should wipe any affected areas by hand. In the case of interdigital tinea pedis, patients should thoroughly wipe each interdigital space. In some embodiments, the bottom and sides of both feet should be wiped. Studies have indicated that this technique is effective at preventing reinfection, as fungi may have imperceptibly infected other parts of the foot, and are later transferred back to the region of the original infection when not treated. Wipes can be packaged with two wipes in a pouch, one for each foot, or one wipe can be used for both feet, as long as the saturation is appropriate for the application.

Benefits of the Wipe Embodiment

Dosing Assistance

In some embodiments, the disposable wipe application provides a greater degree of control over patient dosing, as compared with creams, gels, or sprays. Unlike conventional topical treatments, where patients may use too little (resulting in insufficient drug delivery) or too much (causing their supply of treatment to run out before the end of therapy), an individually packaged wipe provides a correct dose of active ingredients with less possibility for error. Current approaches to tinea pedis treatment often fail due to premature discontinuation of therapy by patients, who may stop using topical treatments once their symptoms have resolved but before the infection is fully eliminated. The compositions using the wipe invention can be packaged in discrete quantities (for example, 28 individual packets for a 4-week course of treatment) rather than one tube with an indeterminate number of doses; thus, patients may be more likely to adhere to a full treatment regime. Embodiments of the invention include packages that have 7 or 14 packets (e.g., wipes), anticipating treatment durations for one or two weeks. Daily administrations are preferred, to minimize overdrying while simultaneously providing the required therapeutic value. Such administrations, which include the antifungal, antiperspirant, and the drying agent, have been found to be therapeutically effective regardless of the stage of the disease at the time treatment is commenced.

Disposable wipes can also assist with pulse therapies. For example, in a four-week antifungal-antiperspirant combination therapy, it could be beneficial to reduce the application of antiperspirant to twice weekly while still applying the antifungal every day. Rather than asking patients to keep track of what drugs to apply on which days, they could be offered 28 individual pouches with the appropriate drugs for each day, labeled with the day of intended use. This enables the patients to conveniently apply the correct medication, and increases the likelihood of adhering to a full course of therapy.

Cleaning Effect

The disposable wipe application takes advantage of friction, an important component of cleansing any surface. Patients tend to apply friction more effectively when they do not make direct contact with the skin. This is due in part to the natural lubrication of oils on the skin, and in part to an understandable hesitance to dig deeply into infected areas. Furthermore, the disposable wipe application decreases the risk of accidental manual transmission by providing a barrier between the hand and the infected foot, which decreases the patient's hesitation in applying the medication, increasing the friction applied and thus cleaning the infected skin.

Convenience and Comfort

Many existing topical antifungal applications, especially topical cream, leave an oily residue on the skin. Many patients find this unpleasant, particularly when they need to put socks and shoes on shortly after application. Because the wipe allows for the drug to be delivered in a liquid solution, rather than requiring a semisolid emulsion like a cream or gel, solvents like ethanol can be used in liquid form. Ethanol is a preferred vehicle, because it evaporates quickly, produces a cooling sensation, and leaves the skin dry. This experience, which many patients find pleasant, contributes to ethanol's popularity in other topical products, including hand sanitizer and aftershave. Likewise, by using ethanol the composition does not leave an oily residue on the hands. Furthermore, the tendency of ethanol to cause a burning sensation is minimized when applied to the foot, because the foot's temperature is lower than the rest of the body (see full explanation of ethanol's effect on TRPV1 in the "Vehicle" section above).

Patient non-compliance is a significant hurdle in the effective treatment of tinea pedis, and the compositions of the present invention increase patient comfort and thus offer a significant improvement over existing therapies since patient compliance is increased. The simple process of opening the package, wiping the feet, and throwing the wipe away mimics the familiar experience of using a moist towelette on one's hands at a restaurant, and the lack of residue left behind on the hands and feet means that patients will be inclined to continue therapy longer than they otherwise might.

Example 1—Exemplary Test Results Using Compositions of the Invention

Initial trials of an embodiment of the invention were conducted with patients suffering from tinea pedis, comparing once-daily application of the invention to the current standard treatment for tinea pedis, twice-daily application of terbinafine cream, as well as a placebo (consisting of a towelette saturated with ethanol, but containing neither an antifungal nor an antiperspirant). Results of the study indicated that once-daily treatment with the invention was similarly effective to twice-daily treatment with terbinafine cream, and significantly more effective than placebo. Thirty (30) patients were treated with each method for 4 weeks, and results were recorded 2 weeks after the conclusion of treatment. A potassium hydroxide preparation was used to test for the presence of fungi. At the conclusion of the study, 21 patients treated with the invention had negative results, compared to 22 patients treated with terbinafine cream. Only 8 patients treated with placebo were negative at the end of the study. Subjective feedback from patients favored the invention. The cream was described as "slippery" and "uncomfortable," and twice-daily application was described as a "hassle," while the invention was described as "very easy to use" and "very effective." One patient said she would be "ecstatic" to see the invention available commercially, while another, at the study's conclusion, declared that this was the "best condition My feet have ever been in."

TABLE 1

Negative KOH After 6 Weeks

| Treatment | Number of Patients with Negative KOH |
|---|---|
| Invention (1x/day) | 21/30 |
| Terbinafine cream (2x/day) | 22/30 |
| Placebo (1x/day) | 7/30 |

These study results indicate that once-daily application of the invention is similarly effective to twice-daily application of terbinafine cream. This increased convenience is particularly salient because poor treatment adherence is a major reason why tinea pedis treatments fail in practice. A treatment that requires less frequent application is more likely to be used for the full treatment period, and thus is more likely to lead to positive outcomes in real-world applications where treatment discontinuation is more likely. The positive response of patients to the treatment also indicates that the treatment would be better received than the current standard treatment. Patients preferred the dry sensation of the invention over the oily cream, and this experiential preference would further improve adherence, and thus outcomes.

This study design was chosen to be in line with standard clinical trials for antifungal treatments for tinea pedis, which use a 4-week course of treatment and require confirmation of fungal infection. As previously discussed, this excludes patients whose fungal infection has been superseded by bacterial infection. For these patients, the invention is likely to be significantly more effective than an antifungal alone.

Example 2—Exemplary Method for Manufacturing the Composition

Ethanol is added to a container, with the volume of ethanol not to exceed 75% of the desired final volume. Terbinafine powder is added to the container and stirred. The mass of terbinafine is added such that the concentration of terbinafine will be about 10 grams per liter of the solution at the desired final volume. Crystalline aluminum chloride hexahydrate is added to the solution, such that the concentration will be about 200 grams per liter of aluminum chloride at the desired final volume. The crystalline aluminum chloride hexahydrate may be crushed before addition to enable faster dissolution. After the terbinafine and aluminum chloride hexahydrate have been added to the solution, more ethanol is added until the volume reaches the desired final volume. The container is sealed to prevent evaporation, and the solid ingredients dissolve to create a uniform solution. Heat and agitation may be introduced to expedite the process of dissolution. A wipe can be saturated with the solution for application by a patient.

Example 3—Treatment and Cost Savings Using the Invention

In certain embodiments, such as a spray or a gel, patients apply the invention directly to the foot. In these cases, the invention has the potential for cost savings over existing treatment since once-daily treatment with the invention achieves the same efficacy as twice-daily treatment with a standard antifungal. The antiperspirant component added to the invention is less expensive to produce than the additional amount of antifungal that is required in twice-daily treatments. Furthermore, because the invention may be more pleasant and more effective than existing treatments, patients are less likely to discontinue treatment early and experience a relapse of the infection, requiring additional treatment. This kind of redundant retreatment is a significant cost in the treatment of tinea pedis, and is reduced by the invention.

Example 4—Consistent Treatment Irrespective of the Stage of the Infection

One advantage of the invention compared to existing treatments for tinea pedis is its ability to treat the infection regardless of the stage of the infection. As previously noted, the simple form of the disease (dermatophytosis simplex) is a purely fungal infection, characterized by dry, flaky skin. When bacteria proliferate in the infected space, supplanting the fungi, the disease is called dermatophytosis complex, and is characterized by more unpleasant symptoms, notably maceration and odor. At this stage of the disease, antifungals alone are less effective since bacteria have become the dominant agent in the infection. Lay knowledge of this distinction is not widespread, and both stages of the disease are recognized as "athlete's foot;" thus, it is likely that a person whose infection has progressed to the dermatophytosis complex stage will seek out a common treatment for athlete's foot, such as an over-the-counter topical antifungal cream, which is unlikely to be effective against this stage of the disease. It may take several unsuccessful treatments, an appointment with a dermatologist, and laboratory work to correctly identify and treat the infection.

This invention is advantageous because it is effective against tinea pedis at any stage in its development. The antifungal eliminates fungi, the antiperspirant and the alcoholic vehicle have antibacterial activity, and the sweat-blocking activity of the antiperspirant and the drying effect of the alcohol lead to a dry environment inimical to fungal and bacterial growth. Patients and clinicians thus benefit from having one treatment that is effective against tinea pedis, regardless of the stage of infection, reducing the possibility of ineffective treatment and the need for diagnostic testing to determine the correct treatment.

Example 5—Treatment of Various Dermatophytoses

This invention is promising for its ability to treat various forms of dermatophytoses. Tinea pedis has been discussed herein at length, but the benefits of an antifungal-antiperspirant combination therapy extend to other dermatophytoses where perspiration can be an exacerbating factor. Tinea cruris (jock itch) affects the groin, which is an ideal environment for fungal growth due to moisture and heat trapped by occlusive clothing. Tinea corporis (ringworm) commonly affects areas where sweat accumulates, such as armpits and abdominal skin folds. Other dermatophytoses, including tinea manuum, are more common among those who sweat excessively. In all of these cases where sweat is a contributing factor to the development and persistence of a fungal infection, antifungal-antiperspirant treatment is advantageous. By reducing sweat, it inhibits conditions favorable to fungal growth, and its activity against a broad spectrum of microorganisms ensures successful treatment of the fungal infection and any opportunistic co-infection that may arise in the weakened stratum corneum.

While the invention has been particularly shown and described with reference to specific preferred embodiments, it should be understood by those skilled in the art that various changes in form and detail may be made therein without departing from the spirit and scope of the invention as defined by the following claims.

I claim:

1. A composition effective in treating tinea pedis, tinea cruris or tinea manuum, the composition comprising
an antifungal present in a pharmaceutically acceptable amount to effectively treat the tinea pedis, tinea cruris or tinea manuum, the antifungal comprising at least one of amorolfine, butenafine, naftifine, terbinafine, tolnaftate or an azole antifungal, or pharmaceutically acceptable salts thereof;
an antiperspirant drying agent that includes an aluminum salt; and
a cream-free solvent vehicle comprising an alcohol for delivery of the antifungal and the drying agent, wherein the composition is a solution and the aluminum salt is present in an amount of between 15 and 20% by weight.

2. The composition of claim 1 wherein the antifungal is terbinafine and the terbinafine is present in an amount of between 0.5 and 10% of the composition by weight.

3. The composition of claim 1 wherein the antiperspirant is $AlCl_3.6H_2O$.

4. A wipe comprising the composition of claim 1, the wipe for application to and treatment of a dermatophytic condition of a patient.

5. A solution for treatment of a dermatophytic infection that includes at least one of tinea pedis, tinea cruris or tinea manuum, the solution produced by the process of:
adding terbinafine to a liquid solvent solution comprising ethanol;
adding a measured amount of crushed crystalline $AlCl_3.6H_2O$ to the solution;
adding makeup solution, if required, to establish a concentration of $AlCl_3.6H_2O$ of between about 150 and 200 gm/liter and a concentration of terbinafine of about 10 gm/liter of the solution; and
dissolving the terbinafine and the $AlCl_3$ to provide a uniform solution.

6. The solution of claim 5 wherein the solution is distributed on a wipe for treatment of a dermatophytic condition of a patient.

7. The solution of claim 5 wherein the terbinafine is a powder.

8. The solution of claim 5 wherein the terbinafine is added in an amount not to exceed about 100 gm/liter.

9. The solution of claim 5 wherein the $AlCl_3$ is added in an amount not to exceed about 300 gm/liter.

10. A method for treatment of a dermatophytic infection that includes at least one of tinea pedis, tinea cruris or tinea manuum, comprising the steps of:
topically applying an antifungal comprising at least one of amorolfine, butenafine, naftifine, terbinafine, tolnaftate or an azole antifungal, or pharmaceutically acceptable salts thereof present in a pharmaceutically acceptable amount;
topically applying an antiperspirant comprising an aluminum salt;
topically applying a cream-free solvent vehicle comprising an alcohol,
wherein the antifungal, the antiperspirant and the solvent vehicle are all applied as a solution during a single administration event, wherein the aluminum salt is present in the solution in an amount between 15 and 20% by weight; and
repeating the administration event not more than daily.

11. The method of claim 10 wherein the application is repeated until the infection is resolved, as measurable by a KOH microscopy test.

12. The method of claim 10 wherein the antiperspirant is aluminum chloride hexahydrate.

13. The method of claim 10 wherein the solvent vehicle consists essentially of ethanol.

14. The method of claim 10 wherein a duration of the treatment is between one and four weeks.

* * * * *